United States Patent [19]

Tanaka et al.

[11] Patent Number: 5,026,350

[45] Date of Patent: Jun. 25, 1991

[54] SET OF DOUBLE NEEDLES FOR INJECTING LIQUID MEDICINE

[75] Inventors: Masataka Tanaka, Togura; Masao Ohto, Togane; Tetsuo Sekine; Hiroshi Takahashi, both of Tokyo; Masaru Maruyama, Togura, all of Japan

[73] Assignee: Hakko Electric Machine Works Co., Ltd., Nagano, Japan

[21] Appl. No.: 358,009

[22] Filed: May 26, 1989

Related U.S. Application Data

[63] Continuation-in-part of Ser. No. 2,993, Jan. 13, 1987, Pat. No. 4,846,799.

[30] Foreign Application Priority Data

Jun. 22, 1988 [JP] Japan ............................... 63-82695[U]

[51] Int. Cl.⁵ ............................................... A61M 5/00
[52] U.S. Cl. ...................................... 604/158; 604/164
[58] Field of Search ................ 604/158, 159, 164–168, 604/264, 272, 281, 283

[56] References Cited

U.S. PATENT DOCUMENTS

| | | |
|---|---|---|
| 2,219,605 | 10/1940 | Turkel ................... 604/164 |
| 2,590,895 | 4/1952 | Scarpellino .............. 604/272 |
| 3,487,834 | 1/1970 | Smith, Jr. et al. .......... 604/165 |
| 3,782,381 | 1/1974 | Winnie ................... 604/164 |
| 3,856,009 | 12/1974 | Winnie ................... 604/164 |
| 4,013,080 | 3/1977 | Froning .................. 604/165 |
| 4,511,356 | 4/1985 | Froning et al. ............ 604/164 |
| 4,682,981 | 7/1987 | Suzuki et al. ............. 604/158 |
| 4,846,799 | 7/1989 | Tanaka et al. ............. 604/158 |

Primary Examiner—Stephen C. Pellegrino
Assistant Examiner—Ralph A. Lewis
Attorney, Agent, or Firm—Lowe, Price, LeBlanc, Becker & Shur

[57] ABSTRACT

A set of double needles for injecting liquid medicine into a patient through a single injection point contains an inner curved needle slidably and rotatably supported within a shorter outer needle. The distal end of the inner needle can protrude from the outer needle to extend sideways, in a controlled direction and extent. The direction in which the inner needle point is inserted into the patient is determined by controllably rotating and engaging a base of the inner needle with respect to a base of the outer needle, with structure provided to prevent unintentional relative rotation of the needles. Liquid medicine may thus be infused into the body of a patient at a number of locations at a preselected depth into the body and within a zone laterally extending from the distal end of the outer needle. The inner needle, which may have a lateral hole at its end, is withdrawable within the outer needle and straightens within the latter during the course of such a withdrawal. A flexible adaptor is provided between the needles and a supply of liquid medicine.

8 Claims, 5 Drawing Sheets

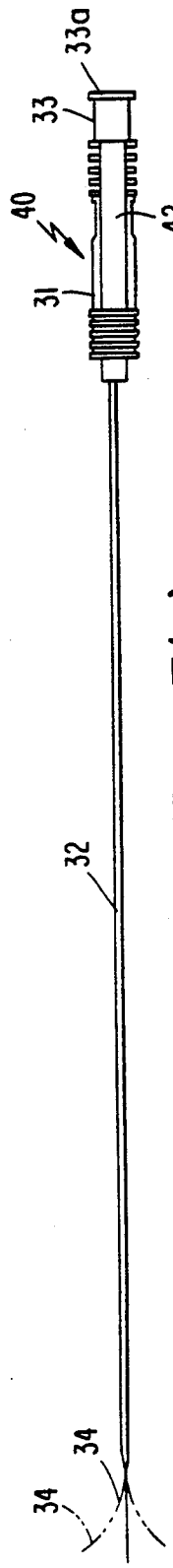
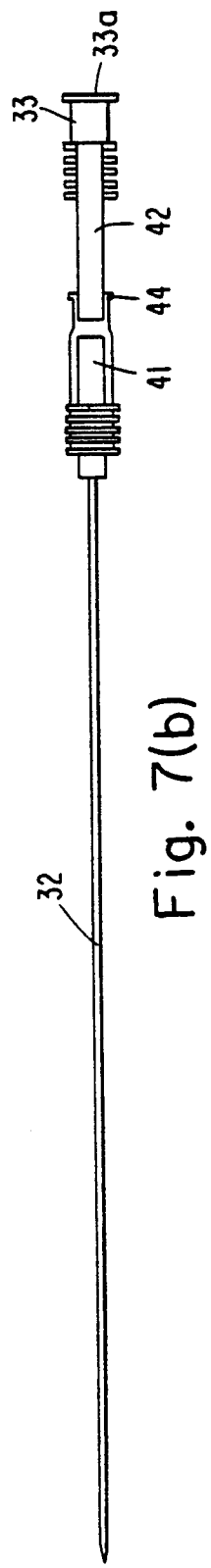
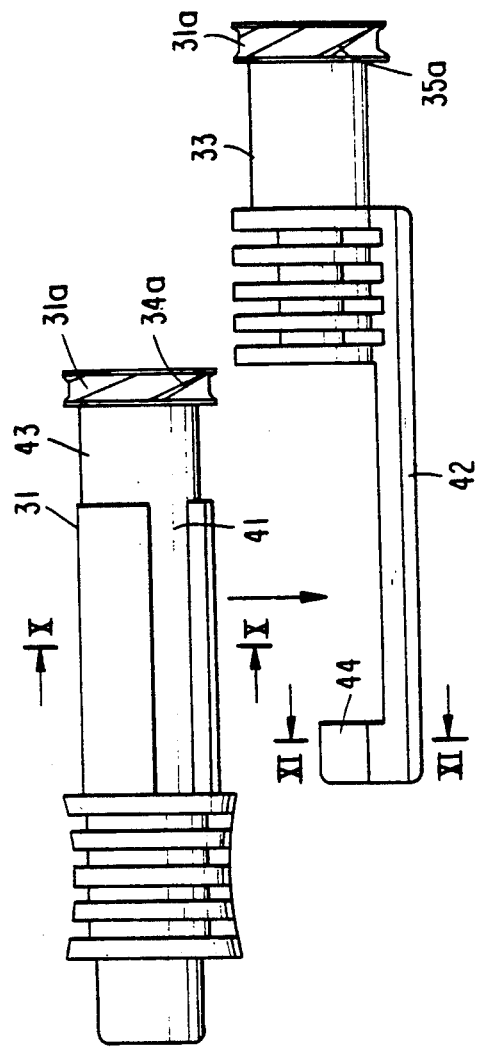
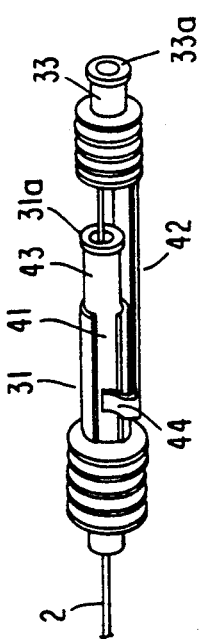

SET OF DOUBLE NEEDLES FOR INJECTING LIQUID MEDICINE

This Application is a Continuation-in-Part of our co-pending Application Ser. No. 07/002,993, filed on Jan. 13, 1987 now U.S. Pat. No. 4,846,799.

TECHNICAL FIELD

The invention relates to a set of double needles for injecting liquid medicine, and more particularly to a set of double needles for injecting liquid medicine by which an injecting point can be varied accurately in a predetermined area in accordance with a single puncture into the skin of the injected body.

BACKGROUND ART

In the conventional technique for injecting a liquid medicine into a patient with a needle, the pain experienced by the patient is increased when more than a single puncturing thereof is needed, e.g., where liquid medicine is injected into a plurality of the affected parts in a predetermined area and where the affected part to be injected is rather large.

In FIGS. 1A to 1C there is shown one type of conventional structure for injecting liquid medicine in which there is provided a set of double needles composed of an inner needle 1 and an outer needle 2 respectively having bevels 1a and 2a and being respectively fixed to bases 3 and 4. FIG. 1A shows the construction of a set of double needles in which the inner needle 1 is adapted to be inserted into the outer needle 2 while FIGS. 1B and 1C show the inner and outer needles 1 and 2 separated from one another.

According to the conventional set of double needles formed per FIG. 1A for injecting liquid medicine, the double needles are punctured together into a human body, to reach the part thereof that is to be medicated by injected liquid medicine. Liquid medicine is thereafter injected into the affected part through the narrower inner needle 1 from the base 3 by which a syringe (not shown) containing the liquid medicine therein is connected. On the other hand, a relatively large amount of liquid medicine may be injected in a short period where a syringe (not shown) containing that amount of the liquid medicine is connected to the base 4 of the wide bore outer needle 2 from which the inner needle 1 is removed as shown in FIG. 1B.

There is, however, a need for a double needle structure where the doctor administering the medicine can exercise precise control at all time during the injecting activity and unintentional relative motions between the inner and outer needles are avoided.

DISCLOSURE OF THE INVENTION

Accordingly, it is an object of this invention to provide a set of double needles for injecting liquid medicine by which liquid medicine is injected into a plurality of the affected parts in a single puncturing of a body in a predetermined area, thereby avoiding an increase in pain for a patient.

It is a further object of the invention to provide a set of double needles for injecting liquid medicine by which an injecting point can be varied in a predetermined area without increasing pain for a patient.

Yet another object of the invention is to provide a set of double needles for injecting liquid medicine, wherein a base part of the inner needle is not subject to unintentional rotation with respect to a base part of the outer needle, so that the direction of the point of the inner needle can be changed accurately with respect to the outer needle.

According to this aspect of the invention, a set of double needles for injecting liquid medicine comprises an inner needle and an outer needle into which the inner needle is inserted rotatably, the inner needle being longer than the outer needle and having a curved distal portion which protrudes from the distal end of the outer needle when fully inserted thereinto, with the curved distal portion adapted to be straightened within the outer needle when retracted in a predetermined length thereof; and a guide means for regulating the rotation of an inner needle base connected to the proximate or base part of the inner needle stepwise by a predetermined angle.

The guide means may comprise a series of guide grooves separated from each other by a predetermined angle and a guide arm which is fixed to the top portion of the inner needle base and slides along at least one of the guide grooves. The guide grooves are formed on the outer surface of the outer needle base attached to the proximate end of the outer needle.

Guide grooves are preferably located at positions separated from each other by a predetermined angle, such as 90°, 120° or 180°. The angle separating the guide grooves determines the angle of change in the direction of projection by the inner needle point, thus the former is selected according to the requirement for the latter. The sliding motion of the guide arm along at least one of the guide grooves described above takes place in cooperation with the sliding motion of the inner needle base within the outer needle base, to prevent rotation of the inner needle base during its sliding motion.

The direction of the inner needle point around the longitudinal axis of the outer needle is changed by the rotation of the inner needle base with respect to the outer needle base. The inner needle is pierced into the diseased part of the body by the projection of the inner needle point out of the outer needle.

The unintentional rotation of the inner needle base is prevented since the guide arm attached thereto slides within the guide groove furnished on the outer needle base.

BRIEF DESCRIPTION OF DRAWINGS

The invention will now be described in accordance with the following drawings wherein.

FIG. 7 is a side elevation view illustrating the entirety of a set of double needles for injecting liquid medicine in another preferred embodiment according to the invention, FIG. 8 is a perspective view illustrating a part of the set of double needles illustrated in FIG. 7, FIG. 9 is a side elevation illustrating exploded parts of the set of double needles illustrated in FIG. 7.

BEST MODE FOR CARRYING OUT THE INVENTION

Figure 2:
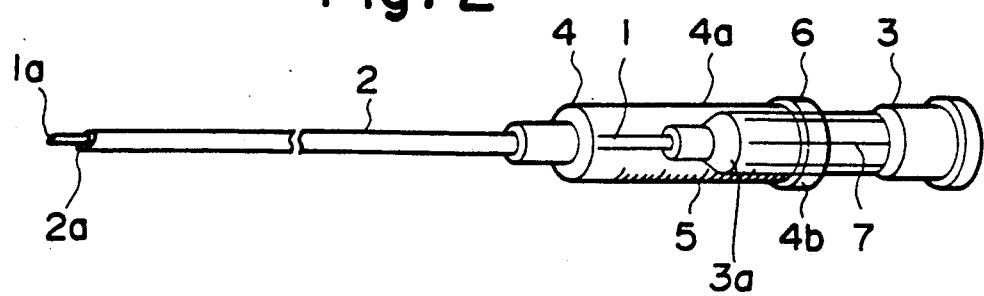
FIG. 2 is a perspective view illustrating a set of double needles for injecting liquid medicine, in the first embodiment according to the invention.

In FIG. 2, there is shown a set of double needles for injecting liquid medicine in the first embodiment according to the invention in which there are provided an inner needle 1 having a curved portion at the distal end thereof and an outer needle 2 into which the inner needle is inserted. The inner and outer needles 1 and 2 are provided with bevels 1a and 2a respectively and the inner needle 1 is longer than the outer needle 2 so that the curved portion of the inner needle 1 protrudes from the outer needle 2 as described later in more detail when the inner needle 1 is fully inserted into the outer needle 2. Further, the inner and outer needles 1 and 2 are fixed to bases 3 and 4 respectively. The base 4 for the outer needle 2 is transparent and comprises a main body 4a having a measuring mark 5 thereon and an end portion 4b having a standard mark 6 thereon. On the other hand, the base 3 for the inner needle 1 is provided with an angle mark 7 thereon.

Figure 3A:
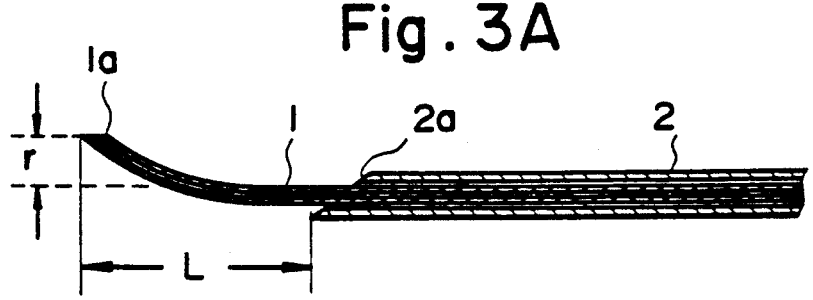
FIGS. 3A to 3C are cross-sectional views each illustrating a relation between the distal ends of an inner and an outer needle in the first embodiment according to the invention.

In operation, the bevel 1a for the inner needle 1 is positioned at the distance 4 from the center line because the inner needle 1 has the curved portion at the distal end thereof when the inner needle 1 protrudes from the bevel 2a for the outer needle 2 in a predetermined length L of, for instance, 25 mm, as shown in FIG. 3A.

Figure 3B:
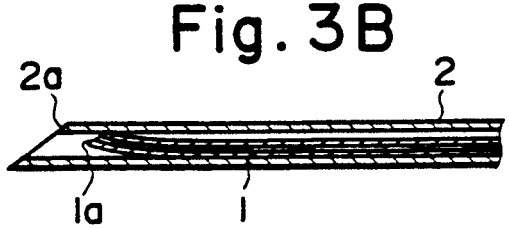

The inner needle 1 is straightened in the outer needle 2 in accordance with the resilient deformation thereof when the bevel 1a of the inner needle 1 is retracted into the outer needle 2 as shown in FIG. 3B. At this stage, the inner needle 1 is rotated by 180° in accordance with the angle mark 7 on the base 3 and the standard mark 6 on the end portion 4b of the base 4.

Figure 3C:
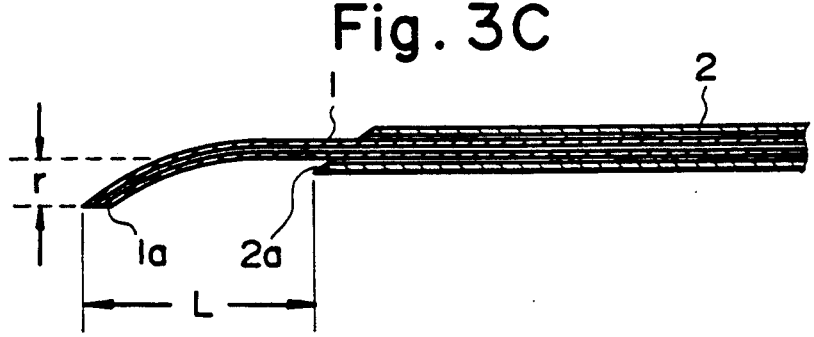

The bevel 1a is positioned at the distance r in the opposite direction from the center line due to the resilience thereof when the inner needle 1 protrudes from the bevel 2a for the outer needle 2 in a predetermined length L mentioned above as shown in FIG. 3C. The protruding length L is adjusted by determining the front end portion 3a for the base 3 in accordance with the measuring mark 5.

Figure 4:
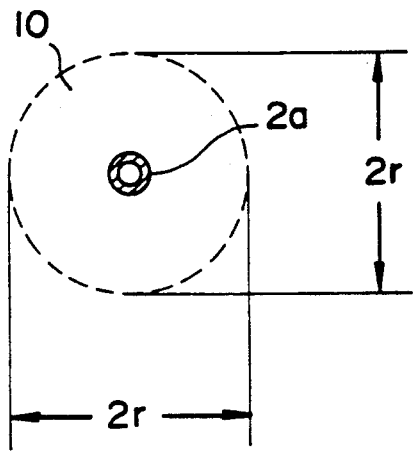
FIG. 4 is an explanatory view showing a covering area in a single puncturing of a set of double needles according to the invention.

It is understood from the explanation as shown in FIG. 4 that liquid medicine is projected to cover a predetermined area 10 having a diameter 2r the center of which is indicated at the bevel 2a for the outer needle 2.

Figure 5A:
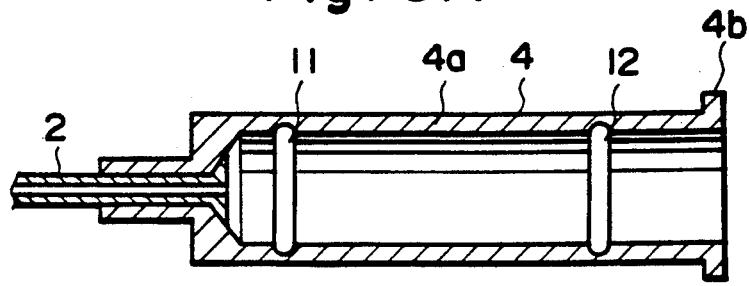
FIG. 5A is a cross-sectional view illustrating a base fixing an outer needle thereto in the second embodiment according to the invention.
Figure 5B:
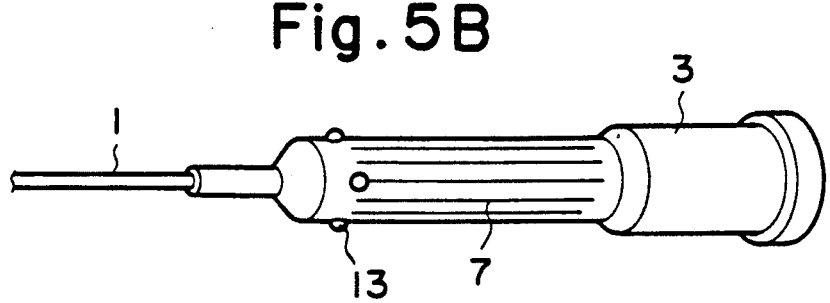
FIG. 5B is a perspective view illustrating a base fixing an inner needle thereto in the second embodiment according to the invention.

In FIGS. 5A and 5B, there is shown a set of double needles for injecting liquid medicine in the second embodiment according to the invention. The double needles are composed of an inner needle 1 which is fixed to a base 3 and an outer needle 2 which is fixed to a base 4. The base 3 is provided with projections 13 thereon each of which is deformed resiliently to be positioned at, for instance, 90 degree intervals while the base 4 is provided with grooves 11 and 12 on the inner surface thereof. In FIGS. 5A and 5B, like reference numerals indicate like parts as in FIG. 2, In operation, the base 3 is positioned inside the base 4 such that the inner needle 1 is inserted into the outer needle 2. At this stage, the projections 13 are engaged into the groove 12 and the base 3 is rotated by a predetermined angle in accordance with the standard mark 6 on the end portion 4b and the angle mark 7 on the base 3. At the next stage, the base 3 is pushed forward so that the projections 13 are compressed whereby the base 3 is moved in a slidable manner inside the base 4 and that the projections 13 are engaged into the groove 11 whereby the base 3 is stopped while the inner needle 1 protrudes from the bevel 2a for the outer needle 2 in a predetermined length L as mentioned before. In the present embodiment, the force of engaging the projections 13 into the groove 11 is slightly greater than that of engaging the projections 13 into the groove 12 so that the handling of the double needles becomes easier.

Figure 6A:
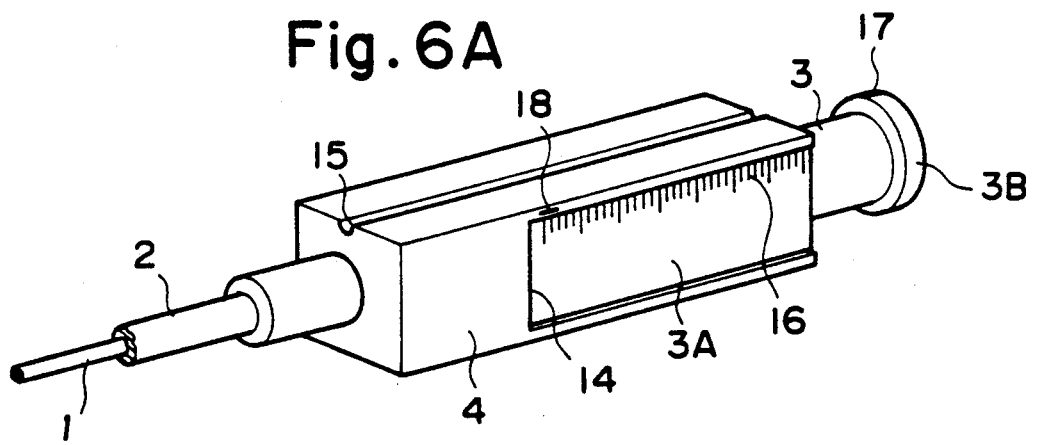
FIG. 6A is a perspective view illustrating a set of double needles for injecting liquid medicine in the third embodiment according to the invention.
Figure 6B:
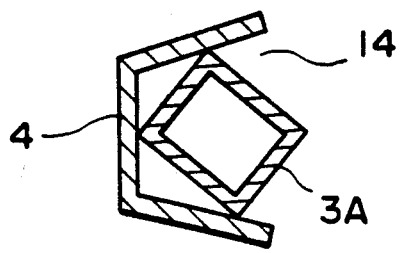
FIGS. 6B and 6C are cross-sectional views each illustrating a relation of bases for inner and outer needles in the third embodiment according to the invention.
Figure 6C:
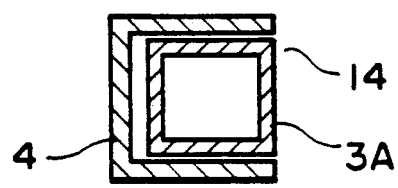

In FIGS. 6A to 6C, there is shown a set of double needles in the third embodiment according to the invention wherein a base 4 for an outer needle 2 is of a square having an opening portion 14 at the side thereof, a slit 15 to be utilized as a standard mark for the rotation at the other side thereof, and a mark 18 to be utilized as a standard point. On the other hand, the base 3 for the inner needle 1 comprises a square portion 3A and a circular portion 3B to which a syringe (not shown) is connected. A measuring mark 16 is provided on the square portion 3A and a standard mark 17 is provided on the circular portion 3B so that the corresponding relation between the inner and outer needles 1 and 2 is known in accordance with the relative positions of the marks 16 and 17 in regard to the slit 15 and mark 18.

In operation, the base 3 is pulled back such that the top edge thereof is positioned at the opening portion 14 whereby the base 3 is rotated as shown in FIG. 6B. In the rotation of the base 3, the base 4 is deformable so that the base 3 can be easily stopped after the rotation of 90°, 180° or 270°. Thereafter, the base 3 is pushed forward so that the inner needle 1 protrudes from the bevel 2a of the outer needle 2 in a predetermined length by checking the measuring mark 16 in regard to the mark 18.

FIG. 7 shows the vertical view of an embodiment that is adapted to ensure controlled and secure rotation/positioning between the inner and outer needles according to a further embodiment of the invention as disclosed and claimed herein and FIG. 8 shows the perspective view of this embodiment. In these figures, the outer needle 32 is attached to the outer needle base 31, which is preferably made of transparent thermoplastic material. The inner needle 34 is attached to the inner needle base 33 placed at the proximate end (at the right in FIGS. 7-9) of the outer needle base 31.

The set of double needles for injection of liquid medicine in this embodiment is composed of the outer needle 32 and the inner needle 34 inserted therein. As in the first embodiment, the inner needle 34 is longer than the outer needle 32 and its distal end part is bent in an appropriate curvature. This curvature of the inner needle 34 causes its distal part to curve outwards with respect to the longitudinal axis of the outer needle 32 when the inner needle 34 is protruded out of the distal end of the outer needle 32.

Thus, the direction of the point of the inner needle 34 is adjusted by rotating the inner needle base 33, which causes the inner needle to rotate around the longitudinal axis, allowing the administration of the liquid medicine in the broad region of the affected part of the patient by way of a single puncture of the needle set into the patient's body.

As shown in FIG. 9, the outer needle base 31 and the inner needle base 33 have, at their proximate portions, the fixing members 31a and 33a provided with threads 34 and 35 on their edges. These fixing members 31a and 33a are inserted into correspondingly threaded portions (not shown) formed at the end of a syringe with which the needle bases are connected by means of the threads 34a and 35a which fit these threaded portions.

In more detail, in the event that injection is performed through the inner needle 34, the fixing member 33a for the inner needle base 33 is connected with the syringe; and in the case where the injection is performed through the outer needle 32, the fixing member 31a is connected with the syringe. Thus, injection either through the inner needle 34 or the outer needle 32 is possible depending on the requirement for the administration of the liquid medicine.

The inner needle 34 is removed from the outer needle 32 for injection solely through the outer needle.

Figure 10:
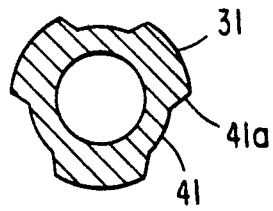
FIG. 10 is a cross-sectional view along the line X—X in FIG. 3 of the set of double needles illustrated in FIG. 9.

The outer needle base 31 and the inner needle base 33 are both provided with cooperating guide means 40 which serves to guide the inner needle with respect to the outer needle, where the direction of the inner needle point is to be controllably and securely changed. The guide means 40 is composed of a plurality of guide grooves 41 formed on the outer surface of the outer needle base 31, and the guide arm 42 formed on the inner needle base 33 extending toward the outer needle base 31. A number of the guide grooves 41 are provided extending along the longitudinal axis of the outer needle base 31 and the grooves are separated from each other by a predetermined angle, for example, 90°, 120°, or 180°. FIG. 10 shows an example in which three guide grooves 41 are formed with an even separation of 120° in the form of recesses on the surface of the outer needle base 31 with skewed side walls 41a.

Figure 11:
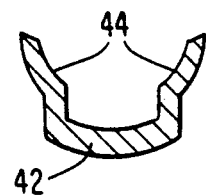
FIG. 11 is a cross-sectional view along the line XI—XI in FIG. 9.

On the surface of the outer needle base 31 at the open end of the guide grooves 41 (the right end in FIG. 9) is formed a neck portion 43 communicating to the guide grooves 41. The tracking portions 44 of the guide arm 42 are in contact with the neck portion 43 during the rotation of the inner needle base 33. The guide arm 42 extends from the distal end of the inner needle base 33 along is axis. The end portion of this extension is bent perpendicularly to the longitudinal axis of the guide arm, so as to form the tracking portions 44 described above. FIG. 11 shows the shape of the tracking portions 44 which are formed as a pair of branches extended from the guide arm 42.

Figure 1A:
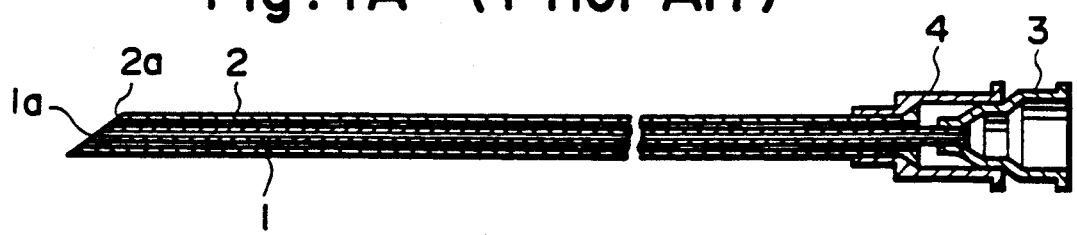
FIG. 1A is a cross-sectional view illustrating a conventional set of double needles for injecting liquid medicine.
Figure 1B:
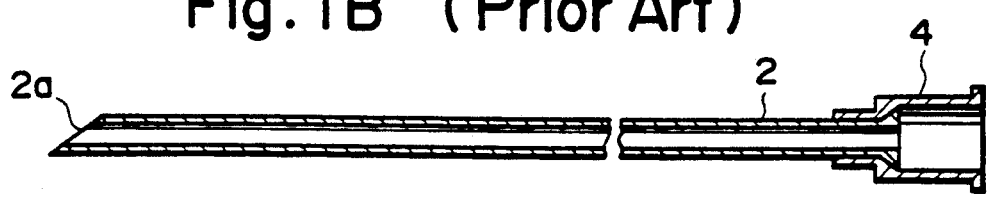
FIG. 1B is a cross-sectional view illustrating an outer needle in FIG. 1A.
Figure 1C:
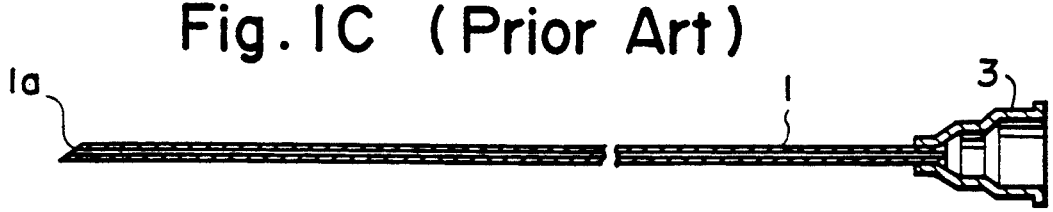
FIG. 1C is a cross-sectional view illustrating an inner needle in FIG. 1A.

A pair of the tracking portions 44 contact slidably with the bottom surfaces of the two guide grooves on the outer needle base 31, pressing them inward, and slide along the guide grooves 41 so as to restrain the inner needle base 33 from unintentional rotation. The tracking portions 44 are curved in such a curvature to have substantially the same shape as the surface of the guide groove 41, whereby the release of the tracking portions 44 from the guide groove 41 is prevented by a resilient and tight contact therebetween. Though a pair of the tracking portions are formed in this embodiment, even a single tracking portion may be used. The operation of changing the direction of the point of inner needle 34 according to the structure described above is explained in the following. The distal part of the inner needle 34 is curved in an appropriate curvature prior to the insertion into the outer needle 32 to keep it straight while contained therein. After the inner needle 34 is inserted sufficiently in the outer needle 32, the distal part of the inner needle 34 projects with a curvature out of the outer needle 32 which is shorter than the inner needle 34 (See FIG. 1).

The change of the direction of the inner needle 34 is effected by drawing back the inner needle base 33, as indicated in FIG. 7(b), and releasing the tracking portions 44 provided at the top of the guide arm 42 from the guide grooves 41 on the outer needle base 31. In this state, the tracking portions 44 are located on the neck portion 43 on the outer needle base 31, leaving the inner needle base 33 rotatable with respect to the outer needle base 31. Therefore, moving the tracking portions 44 to the position aligned with the adjacent guide grooves 41 through rotation of the inner needle base 33, and then pushing the inner needle base 33 toward the outer needle base 31 enables the user to selectively protrude the inner needle 34 from the outer needle 32 (See FIG. 7(a)). The inner needle base 33 does not rotate at all during this procedure, because the tracking portions 44 of the guide arm 42 slide within the mating guide grooves 41. Therefore, the point of the inner needle 34 is pierced accurately to the desired position in the diseased part of the patient's body, where the liquid medicine is administrated without an error.

Figure 12:
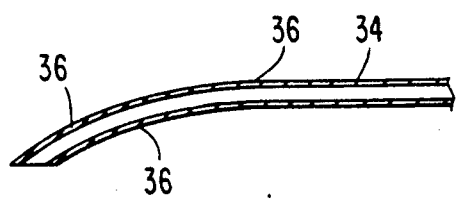
FIG. 12 is a cross-sectional view illustrating an inner needle of another embodiment of the invention.

FIG. 12 shows a modification of the inner needle 34 wherein a plurality of outlets 36 for liquid medicine is provided at the curved distal portion. By such a structure, the liquid medicine is ejected not only from the needle points but also from the outlets 36, making it possible to inject liquid medicine in more extended range.

Figure 13:
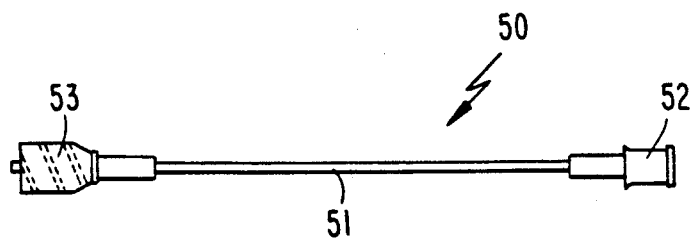
FIG. 13 is a side elevation illustrating an adaptor applicable to the invention.

FIG. 13 shows an adaptor 50 disposed optionally between the syringe and the double needles. The adaptor 50 consists of the conduit portion 51 and the joints 52 and 53 attached to the ends of the conduit portion 51, all preferably made of flexible thermoplastic materials. The joint 52 of the adaptor 50 is connected to the threaded part of a syringe, while the joint 53 is connected to the fixing member 31a or 33a of the needle base 31 or 33, respectively, communicating these elements. Provided that such an adaptor 50 is formed to have a predetermined flexible body length 51, a syringe placed remote from the needles need not be placed stationarily, hence the versatility of the apparatus for use in a variety of circumstances is greatly improved.

The set of double needles according to the second embodiment of the present invention, which is furnished with a guide means consisting of a plurality of guide grooves and a guide arm capable of sliding within these grooves, is free from problems caused by unintentional rotation of the inner needle associated with the axial movement thereof, so that changing the direction of the curved inner needle accurately and readily is made possible.

Although the invention has been described with respect to specific embodiments for complete and clear disclosure, the appended claims are not be thus limited but are to be construed as embodying all modification and alternative construction that may occur to one skilled in the art which fairly fall within the basic teaching herein set forth.

We claim:

1. Apparatus for injecting liquid medicine at each of a plurality of user-selected nearby locations through a common entry point of the injected body, comprising:

an inner needle, and an outer needle into which said inner needle is slidably and rotatably inserted, each of said needles having a sharp distal end and a proximate end formed for selectively communicating with a source of liquid medicine for pressurized injection thereof into said injected body at a selected first location of said body for injection through said sharp distal end of said outer needle and at a plurality of selected second locations in said body through said sharp distal end of said inner needle;

said inner needle being longer than said outer needle and having a curved portion at the distal end thereof which protrudes from the distal end of said outer needle when fully inserted thereinto, said inner and outer needles cooperating such that said curved portion of said inner needle is straightened within said outer needle when retracted therein and said inner and outer needles are then rotatable to different angular disposition relative to each other for subsequent reinsertion of said inner needle into said outer needle to thereby locate the sharp distal end of said inner needle at a selected other one of said plurality of second locations for injection of said liquid medicine thereat;

said apparatus further comprising an inner needle base fixed to the proximate end of said inner needle, an outer needle base fixed to the proximate end of said outer needle, and a guide means for regulating the rotation of said inner needle base stepwise by a predetermined angle, wherein said guide means comprises a plurality of longitudinally formed guide grooves formed on the outer surface of said outer needle base and a guide arm which is fixed on the inner needle base to extend adjacent to and along the inner needle and is capable of sliding along at least one of said guide grooves engaged therewith, said guide grooves being distant form each other by a predetermined angle and said guide means further comprises a neck portion formed around the outer surface of said outer needle base adjacent and connected to said guide grooves with said guide arm being capable of sliding around said neck portion.

2. The apparatus for injecting liquid medicine according to claim 1, wherein:
said predetermined angle is selected from the group consisting of 90°, 120° and 180°.

3. The apparatus of claim 2, further comprising:
adaptor means for flexibly connecting a syringe supplying liquid medicine and said set of double needles receiving said supplied liquid medicine, said adaptor means having a first joint portion adapted to securely connect to said syringe and a second joint portion adapted to be in communication with one of said inner and outer needle bases, with a predetermined flexible length between said first and second joint portions to enable flow of said liquid medicine therebetween.

4. The apparatus for injecting liquid medicine according to claim 1, wherein:
said inner needle is formed to have a lateral through aperture near its distal end to enable injection of said liquid medicine therethrough.

5. The apparatus of claim 4, further comprising:
adaptor means for flexibly connecting a syringe supplying liquid medicine and said set of double needles receiving said supplied liquid medicine, said adaptor means having a first joint portion adapted to securely connect to said syringe and a second joint portion adapted to be in communication with one of said inner and outer needle bases, with a predetermined flexible length between said first and second joint portions to enable flow of said liquid medicine therebetween.

6. The apparatus of claim 1, further comprising:
adaptor means for flexibly connecting a syringe supplying liquid medicine and said set of double needles receiving said supplied liquid medicine, said adaptor means having a first joint portion adapted to securely connected to said syringe and a second joint portion adapted to be in communication with one of said inner and outer needle bases, with a predetermined flexible length between said first and second joint portions to enable flow of said liquid medicine therebetween.

7. The apparatus for injecting liquid medicine according to claim 2, wherein:
said inner needle is formed to have a lateral through aperture near its distal end to enable injection of said liquid medicine therethrough.

8. The apparatus of claim 7, further comprising:
adaptor means for flexibly connecting a syringe supplying liquid medicine and said set of double needles receiving said supplied liquid medicine, said adaptor means having a first joint portion adapted to securely connect to said syringe and a second joint portion adapted to be in communication with one of said inner and outer needle bases, with a predetermined flexible length between said first and second joint portions to enable flow of said liquid medicine therebetween.

* * * * *